US009326895B1

(12) United States Patent
Winey

(10) Patent No.: US 9,326,895 B1
(45) Date of Patent: May 3, 2016

(54) PROTECTIVE NAPKIN

(76) Inventor: James M. Winey, North Oaks, MN (US)

( * ) Notice: Subject to any disclaimer, the term of this patent is extended or adjusted under 35 U.S.C. 154(b) by 2278 days.

(21) Appl. No.: 12/251,532

(22) Filed: Oct. 15, 2008

Related U.S. Application Data

(63) Continuation-in-part of application No. 11/349,825, filed on Feb. 8, 2006, now abandoned.

(60) Provisional application No. 60/651,847, filed on Feb. 10, 2005, provisional application No. 60/661,570, filed on Mar. 14, 2005.

(51) Int. Cl.
*A61F 13/15* (2006.01)
*A61F 13/20* (2006.01)
*A61F 13/53* (2006.01)
*A61F 13/56* (2006.01)

(52) U.S. Cl.
CPC *A61F 13/15* (2013.01); *A61F 13/53* (2013.01)

(58) Field of Classification Search
CPC ......... A61F 13/15; A61F 13/20; A61F 13/53; A61F 13/55; A61F 13/56
USPC ................................ 604/387, 389, 390; 24/7
See application file for complete search history.

(56) References Cited

U.S. PATENT DOCUMENTS

| | | | | |
|---|---|---|---|---|
| 1,391,121 | A | * | 9/1921 | Keppel .............. 2/49.5 |
| 1,864,281 | A | * | 6/1932 | Short .................. 24/7 |
| 2,081,095 | A | * | 5/1937 | Mull ............... 248/467 |
| 2,247,372 | A | * | 7/1941 | Hart .................... 24/8 |
| 2,287,717 | A | * | 6/1942 | Barnes ................ 24/8 |
| 2,425,635 | A | * | 8/1947 | Nitzberg ............. 2/75 |
| 2,471,331 | A | * | 5/1949 | Lee .................... 2/48 |
| 2,713,686 | A |   | 7/1955 | Oster et al. |
| 2,803,574 | A | * | 8/1957 | Payant ............. 428/78 |
| 3,014,580 | A | * | 12/1961 | Brody et al. ..... 206/447 |
| 3,350,720 | A | * | 11/1967 | Freund ............... 2/48 |
| 3,398,438 | A | * | 8/1968 | Fried et al. .......... 24/7 |
| 3,398,439 | A | * | 8/1968 | Fried et al. .......... 24/7 |
| 3,490,864 | A | * | 1/1970 | Witzig ............. 24/659 |
| 3,675,274 | A | * | 7/1972 | Fried et al. ...... 24/67 R |
| 3,703,149 | A |   | 11/1972 | George |

(Continued)

FOREIGN PATENT DOCUMENTS

| | | |
|---|---|---|
| EP | 1 342 422 | 9/2003 |
| JP | 411 346 894 | 12/1999 |

OTHER PUBLICATIONS

Translation of JP11346894 Dec. 21, 1999; Translation date Aug. 9, 2011.*

*Primary Examiner* — Tatyana Zalukaeva
*Assistant Examiner* — Ilya Treyger
(74) *Attorney, Agent, or Firm* — Sherill Law Offices, PLLC

(57) ABSTRACT

A method of protecting an article of clothing with a napkin. The method includes the steps of (a) obtaining a napkin having (i) an area coated with a pressure sensitive adhesive on a first major surface of the napkin proximate the periphery of the napkin, (ii) a release liner overlaying the pressure sensitive adhesive, and (iii) an aperture through at least the pressure sensitive adhesive and the release liner configured and arranged to accommodate passage of a button therethrough, and (b) selectively securing the napkin to an article of clothing worn by a person by either (i) inserting a button affixed to the article of clothing through the aperture in the tab and through that area of the napkin overlying the aperture, or (ii) removing the release liner and adhesively securing the napkin to the article of clothing.

6 Claims, 3 Drawing Sheets

(56) References Cited

U.S. PATENT DOCUMENTS

| | | | | |
|---|---|---|---|---|
| 3,978,553 A | * | 9/1976 | Honig | 24/7 |
| 4,245,630 A | * | 1/1981 | Lloyd et al. | 604/358 |
| 4,330,888 A | | 5/1982 | Klepfer | |
| 4,420,519 A | * | 12/1983 | Slemmons | 428/41.7 |
| 4,523,333 A | | 6/1985 | Spangler | |
| 4,558,888 A | * | 12/1985 | Hanson et al. | 281/23 |
| 4,562,102 A | * | 12/1985 | Rabuse et al. | 428/43 |
| 4,664,106 A | * | 5/1987 | Snedeker | 602/57 |
| 4,961,666 A | * | 10/1990 | Pitts et al. | 402/79 |
| 5,130,185 A | * | 7/1992 | Ness | 428/41.9 |
| 5,153,040 A | * | 10/1992 | Faasse, Jr. | 428/41.5 |
| 5,658,631 A | * | 8/1997 | Bernstein et al. | 428/42.1 |
| 5,913,478 A | | 6/1999 | Ochsman | |
| 5,933,922 A | | 8/1999 | Ochsman | |
| 6,013,146 A | * | 1/2000 | Yuan et al. | 156/89.22 |
| 6,021,521 A | | 2/2000 | Baratta | |
| 6,021,550 A | * | 2/2000 | Welch | 24/7 |
| 6,097,291 A | * | 8/2000 | Tsai et al. | 340/572.6 |
| 6,122,771 A | * | 9/2000 | Cook et al. | 2/48 |
| 6,149,614 A | * | 11/2000 | Dunshee et al. | 602/57 |
| 6,197,396 B1 | * | 3/2001 | Haas et al. | 428/40.1 |
| 6,403,191 B1 | * | 6/2002 | Casagrande | 428/42.2 |
| 6,420,008 B1 | * | 7/2002 | Lewis et al. | 428/78 |
| 6,706,940 B2 | * | 3/2004 | Worthley | 602/57 |
| 2001/0033915 A1 | * | 10/2001 | Ehmann et al. | 428/195 |
| 2002/0021002 A1 | * | 2/2002 | Finke et al. | 283/81 |
| 2002/0125165 A1 | * | 9/2002 | Russell | 206/447 |
| 2002/0192465 A1 | * | 12/2002 | Liu et al. | 428/354 |
| 2002/0197434 A1 | * | 12/2002 | Rosenbaum et al. | 428/41.8 |
| 2003/0167549 A1 | | 9/2003 | Bourne | |
| 2005/0238836 A1 | * | 10/2005 | Hodsdon | 428/40.1 |
| 2007/0071931 A1 | * | 3/2007 | Schalk et al. | 428/40.1 |

\* cited by examiner

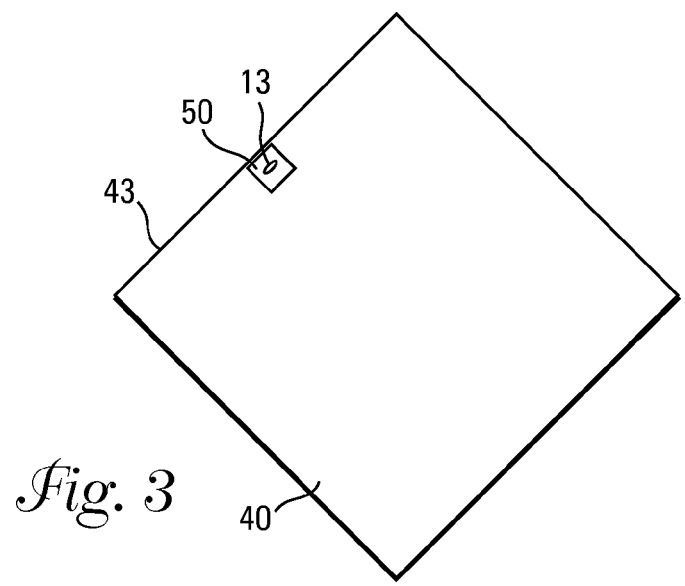
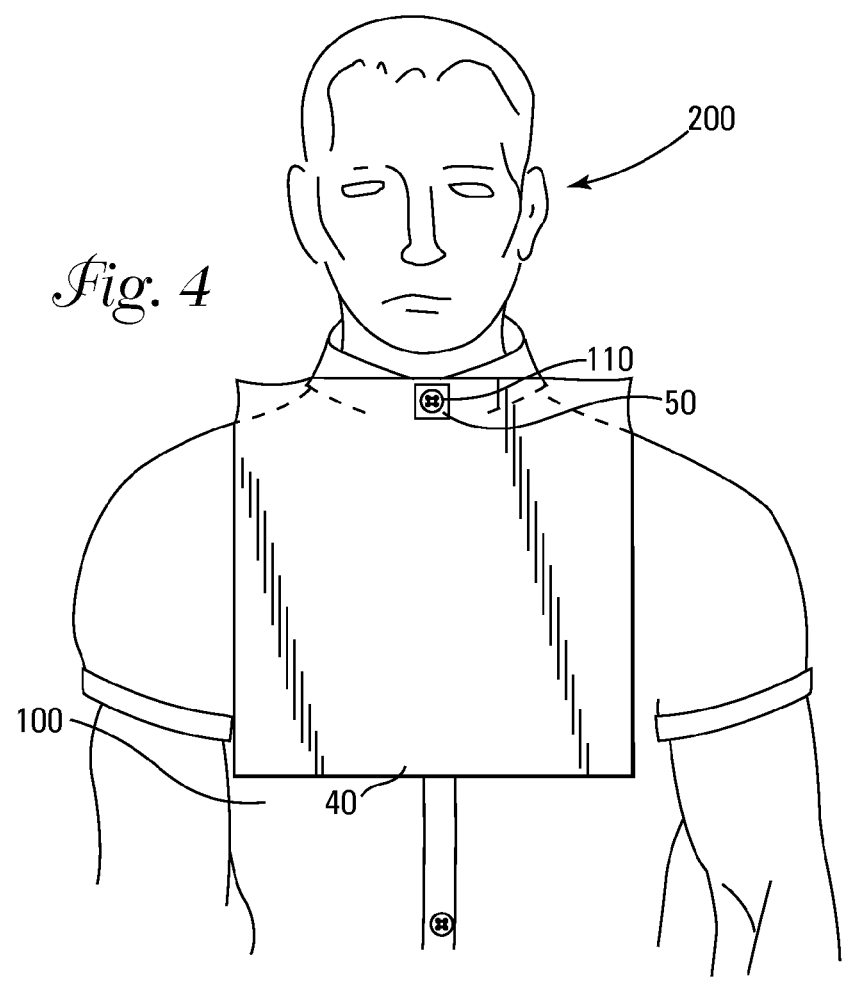

PROTECTIVE NAPKIN

This application is a continuation-in-part of U.S. application Ser. No. 11/349,825 filed on Feb. 8, 2006, which claims the benefit of U.S. Provisional Application No. 60/651,847, filed on Feb. 10, 2005 and U.S. Provisional Application No. 60/661,570, filed on Mar. 14, 2005.

FIELD OF INVENTION

This invention relates to an article of commerce and a method of protecting clothing from food spills and splatters.

BACKGROUND

Most people have experienced that moment when they are dining and food drips or splashes on their clothes. The food is often hard or impossible to remove at that time if the person is outside of his or her home. The clothes are then soiled for the rest of the outing or even permanently. Bibs secured around the neck by ties, adhesive, or Velcro® are well known in the industry. Often the use of such a bib is for children. Such bibs may also be used by adults.

To protect clothing using a bib, a bib would need to be brought along or provided by an establishment. Many establishments do not provide bibs for children or adults. Bringing a bib along is the next best option. But if the bib is forgotten at home this option does not help the unfortunate diner who needs one. Furthermore, bringing along a bib requires a place to store the bib in transit. One's outfit or circumstances may prohibit transporting a bib (for example, no pockets or bag to put a bib into for carrying). But even if a bib is available, many children and adults would not wear a more traditional looking bib.

One other option is to just tuck a portion of a napkin in the collar of one's shirt. This is often hard to accomplish with many shirts and does not allow you to control the area protected by the napkin. This method of protecting one's clothing is also often not looked well upon in some dining establishment or thought to not be good manners by many people.

A solution to the use of a bib tied around the neck or stuffing a napkin in one's shirt is offered by U.S. Pat. No. 5,933,922 (922). The '922 patent discloses a multipurpose clamp that may be affixed to a shirt with one end and holds a portion of a napkin in the other end. While effective in providing protection to the front of a shirt, the method requires having an appropriate clip that may be unsightly, hard to find, or expensive to obtain. Furthermore, the clip may stress the button connection to the shirt due to the weight of the clip.

What is clearly needed is an inexpensive, easily used, light weight, and easily carried method of protecting one's clothes from being soiled while consuming food and beverages.

SUMMARY OF THE INVENTION

A first aspect of the invention is a method of protecting an article of clothing with a napkin, comprising the steps of (a) obtaining a napkin having (i) an area coated with a pressure sensitive adhesive on a first major surface of the napkin proximate the periphery of the napkin, (ii) a release liner overlaying the pressure sensitive adhesive, and (iii) an aperture through at least the pressure sensitive adhesive and the release liner configured and arranged to accommodate passage of a button therethrough, and (b) selectively securing the napkin to an article of clothing worn by a person by either (i) inserting a button affixed to the article of clothing through the aperture in the tab and through that area of the napkin overlying the aperture, or (ii) removing the release liner and adhesively securing the napkin to the article of clothing.

A second aspect of the invention is a napkin having (A) an area coated with a pressure sensitive adhesive on a first major surface of the napkin proximate the periphery of the napkin, (B) a release liner overlaying the pressure sensitive adhesive, and (C) an aperture through at least the pressure sensitive adhesive and the release liner configured and arranged to accommodate passage of a button therethrough. The napkin may be selectively secured to an article of clothing worn by a person by either (i) inserting a button affixed to the article of clothing through the aperture and through that area of the napkin overlying the aperture, or (ii) removing the release liner and adhesively securing the napkin to the article of clothing.

BRIEF DESCRIPTION OF THE DRAWINGS

FIG. 3 is a plan view of a second embodiment of the invention with the attachment area centrally positioned along one edge of the napkin.

FIG. 4 is a plan view of the napkin shown in FIG. 3 adhesively secured to an article of clothing being worn by a person.

DETAILED DESCRIPTION OF A PREFERRED EMBODIMENT

Nomenclature

Figure 1:
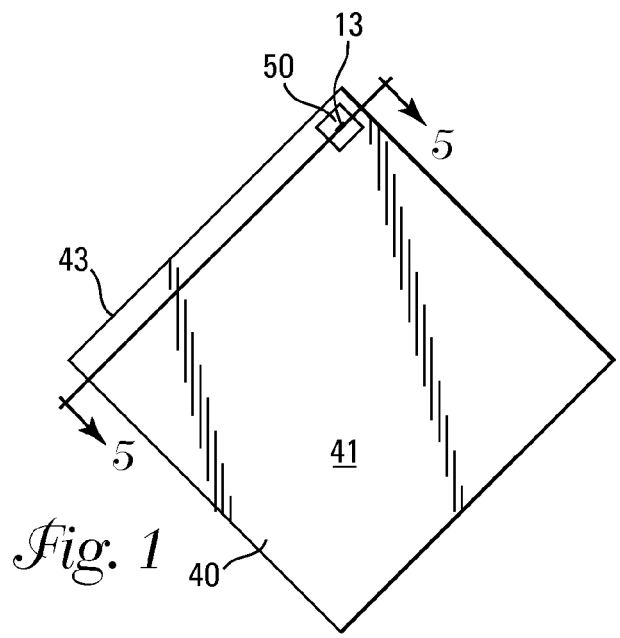
FIG. 1 is a plan view of one embodiment of the invention with the attachment area positioned in a corner of the napkin.

10 Substrate
11 First Major Surface of Substrate
12 Second Major Surface of Substrate
13 Aperture
21 First Layer of Pressure Sensitive Adhesive ("1$^{st}$ PSA Layer")
22 Second Layer of Pressure Sensitive Adhesive (2$^{nd}$ PSA Layer)
30 Release Liner
40 Napkin
41 First Major Surface of Napkin
42 Second Major Surface of Napkin
43 Edge of Napkin
44 Folded Corner of Napkin
50 Attachment Area on Napkin
100 Article of Clothing/Shirt
110 Button
200 Person
I Longitudinal Direction

Definitions

As utilized herein, including the claims, an "aperture" refers to an opening or open space, such as a hole, slit, slot, or notch.

Construction

As shown in FIGS. 1-4, the invention is a protective napkin 40 with an area 50 on a first major surface 41 of the napkin 40 proximate an edge 43 of the napkin 40 (hereinafter referenced as the "attachment area") having both (i) a layer of a pressure sensitive adhesive 22 which may be selectively exposed for adhesively securing the napkin 40 to an article of clothing 100, and (ii) an aperture 13 configured and arranged to serve as a button hole for securing the napkin 40 to an article of clothing 100 via a button 110 on the article of clothing 100. By providing both a pressure sensitive adhesive 22 and a button hole 13 on a napkin 40, a restaurant need only stock and supply a single style of napkin 40 to its patrons, allowing the patron to select between the more secure option of attaching the napkin 40 to the patron's shirt 100 by inserting a button 110 on the shirt 100 through the button hole 13, or the more flexible option of attaching the napkin 40 to the patron's shirt 100 by exposing the adhesive 22 and adhesively attaching the napkin 40 to the shirt 100 at any desired location.

Figure 5:
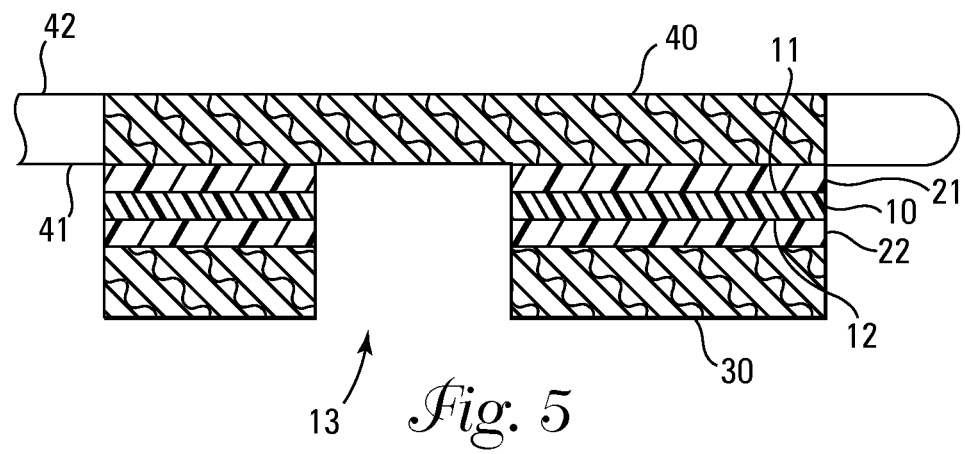
FIG. 5 is an enlarged cross-sectional view of the adhesive area on the napkin shown in FIG. 1, taken along line 5-5.

As shown in FIG. 5, one embodiment of the attachment area 50 includes a substrate 10 with a first layer of a pressure sensitive adhesive ("1$^{st}$ PSA Layer") 21 coated onto a first major surface 11 of the substrate 10 and a second layer of a pressure sensitive adhesive ("2$^{nd}$ PSA Layer) 22 coated onto a second major surface 12 of the substrate 10. The 1$^{st}$ PSA layer 21 is affixed to a first major surface 11 of the substrate 10. The 2$^{nd}$ PSA layer 22 is affixed to a second surface 12 of the substrate 10. Double stick tape is an example of such a substrate 10. A release liner 30 may cover the 2$^{nd}$ PSA layer 22.

An aperture 13 is provided through the substrate 10, the pressure sensitive adhesive layers 21 and 22, and the release liner 30. The aperture 13 preferably also extends completely through the napkin 40 from the first major surface 41 to the second major surface 42 of the napkin 40. The aperture 13 is configured and arranged to accommodate passage of a button 110 therethrough.

The substrate 10 may be made from any suitable material. Substrates 10 coated on both major surfaces 11 and 12 with a PSA layer 21 and 22 respectively, are well known in the industry. The shape of the attachment area 50 may be any suitable size to be affixed on the napkin 40, such as a polygon, a circle, a sector of a circle, a segment of a circle, an ellipse, a sector of an ellipse, and a segment of an ellipse. The preferred shape is a square. The size of the attachment area 50 may be any suitable and appropriate size to allow it to be affixed to the napkin 40. Preferably the attachment area 50 has at least an approximate area of 0.0625 square inches. The most preferred size is approximately 1 square inch.

Any suitable PSA may be used. The 1$^{st}$ PSA layer 21 should be selected to ensure that the napkin 40 remains securely affixed to the napkin 40 during use. The 2$^{nd}$ PSA layer 22 can be any suitable composition capable of providing releasable attachment of the napkin 40 to an article of clothing 100 while preventing the napkin 40 from becoming dislodged during use. A hot melt adhesive (not shown) may also be used.

The 2$^{nd}$ PSA layer 22 may be covered with any suitable release liner 30. Suitable release liners 30 are known and available in the industry. The method of affixing a release liner 30 to a PSA layer 22 is well known in the industry.

Substantially any type and size of napkin 40 may be used. The napkin 40 selection may also depend on the use it will be put to by the user 200. The preferred type of napkin 40 is a disposable napkin 40. The shape may be any suitable shape allowing the desired area of clothing 100 to be covered, such as a polygon, a circle, a sector of a circle, a segment of a circle, an ellipse, a sector of an ellipse, and a segment of an ellipse. The preferred shape is a square or rectangular. The size may be any suitable size allowing the desired area of clothing 100 to be covered. The preferred size is approximately 64 square inches. The most preferred size is 255 square inches. Any suitable thickness of napkin 40 may be used. The preferred thickness is single-ply napkin.

The type of napkin 40 should allow a penetration through the napkin 40 to allow a button 110 on the piece of clothing 100 inserted through the aperture 13 to penetrate the napkin 40. For easier use a stronger or thicker napkin 40 may contain a pre-formed aperture 13 aligned with the aperture 13 through the substrate 10, PSA layers 21 and 22 and release liner 30.

The aperture 13 may be any suitable shape or configuration allowing a button 110 from a piece of clothing 100 to be inserted. Preferably the aperture 13 is an elliptical hole. The size of the aperture 13 may be any suitable size to allow a button 110 from a piece of clothing 100 to be inserted and not compromise the integrity of the substrate 10. Preferably the aperture 13 provides approximately a 0.25 inch opening in the substrate 10 approximately 1 square inch in size.

Method Process

The napkin 40 may be used to protect the front of a person's 200 clothing 100 from being soiled. One of the most common uses for a napkin 40 is to protect a person's 200 clothing 100 from food and beverage spills while eating. The shirt front (unnumbered) is a frequently soiled article of clothing 100. Therefore, the remainder of this discussion will be based upon affixing the napkin 40 to a person's 200 shirt front, but the method of use may be used for any article of clothing 100.

Figure 2:
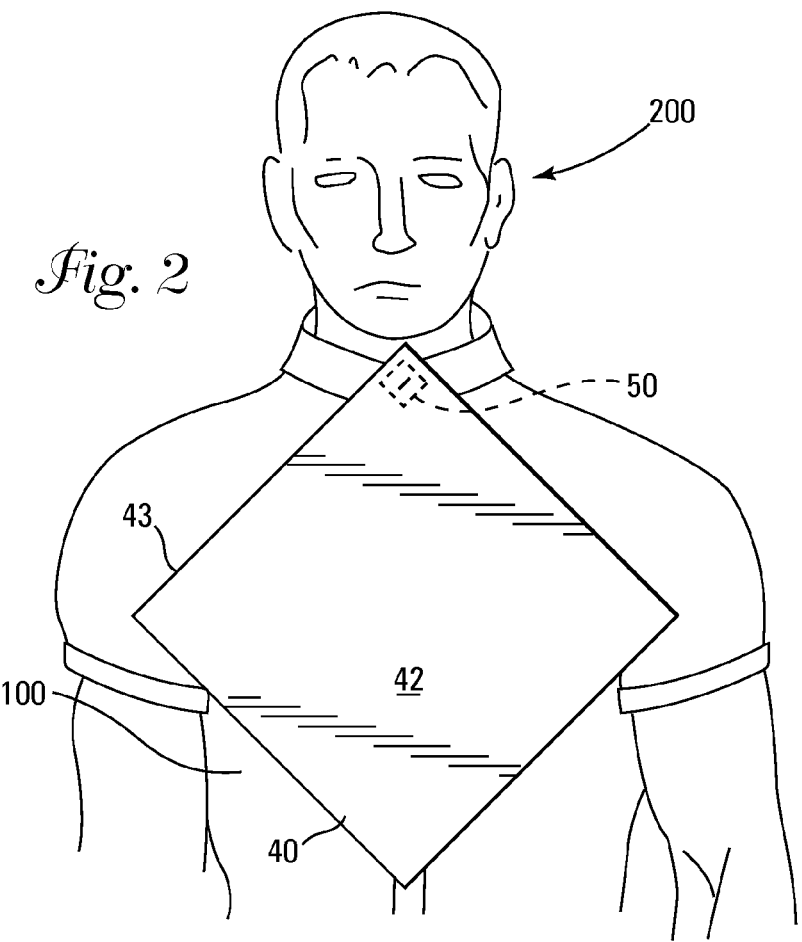
FIG. 2 is a plan view of the napkin shown in FIG. 1 adhesively secured to an article of clothing being worn by a person.

The napkin 40 may be attached to a shirt front by either (i) removing the release liner 30 to expose the 2nd PSA layer 22, and adhesively attaching the exposed 2$^{nd}$ PSA layer 22 to the shirt front as shown in FIG. 2, or (ii) leaving the release liner 30 on the napkin 40 and inserting a button 110 on the shirt front through the aperture 13 as shown in FIG. 4.

Figure 6:
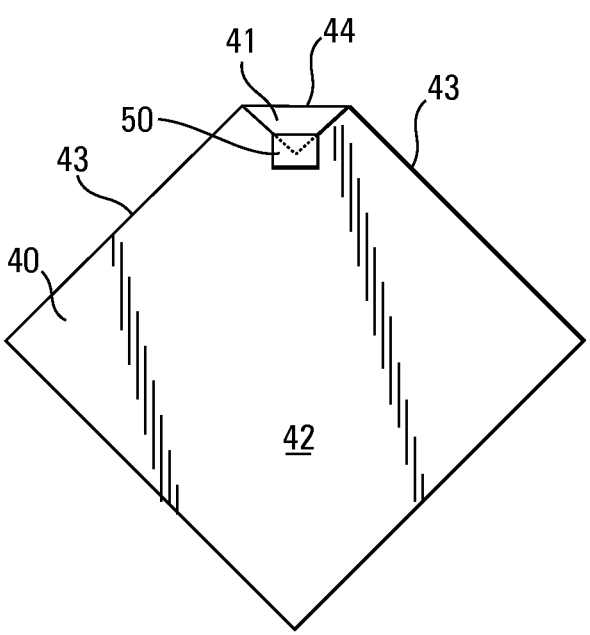
FIG. 6 is a plan view of a third embodiment of the invention with the attachment area positioned over a folded corner of the napkin.

As shown in FIG. 6, when a multi-ply napkin 40 is used a corner (not numbered) of the napkin 40 may be folded over onto the napkin 40, to form a fold 44 and the PSA coated substrate 10 affixed to the napkin 40 to hold down the fold 44 so that the substrate 10 is adhesively attached to both plys.

I claim:

1. A method, comprising the steps of:
   (a) obtaining a napkin having (i) an area coated with a pressure sensitive adhesive on a first major surface of the napkin proximate the periphery of the napkin, (ii) a release liner overlaying the pressure sensitive adhesive, and (iii) an aperture through at least the pressure sensitive adhesive and the release liner configured and arranged to accommodate passage of a button therethrough; and
   (b) selectively securing the napkin to an article of clothing worn by a person by either (i) inserting a button affixed to the article of clothing through the aperture in the pressure sensitive adhesive and the release liner and through that area of the napkin overlying the aperture in the pressure sensitive adhesive and the release liner, or (ii) removing the release liner and adhesively securing the napkin to the article of clothing.

2. The method of claim 1, wherein the aperture extends through the napkin.

3. The method of claim 1, wherein the napkin is disposable.

4. An article of commerce, comprising:
   (a) a napkin having (i) an area coated with a pressure sensitive adhesive on a first major surface of the napkin proximate the periphery of the napkin, (ii) a release liner overlaying the pressure sensitive adhesive, and (iii) an aperture through at least the pressure sensitive adhesive and the release liner configured and arranged to accommodate passage of a button therethrough;

(c) whereby the napkin may be selectively secured to an article of clothing worn by a person by either (i) inserting a button affixed to the article of clothing through the aperture and through that area of the napkin overlying the aperture, or (ii) removing the release liner and adhesively securing the napkin to the article of clothing.

5. The article of claim 4, wherein the aperture extends through the napkin.

6. The article of commerce in claim 4, wherein the napkin is disposable.

\* \* \* \* \*